(12) United States Patent
Daniels et al.

(10) Patent No.: US 10,969,379 B2
(45) Date of Patent: Apr. 6, 2021

(54) NANOPOROUS BIOELECTROCHEMICAL SENSORS FOR MEASURING REDOX POTENTIAL IN BIOLOGICAL SAMPLES

(71) Applicants: THE REGENTS OF THE UNIVERSITY OF MICHIGAN, Ann Arbor, MI (US); Virginia Commonwealth University, Richmond, VA (US)

(72) Inventors: Rodney C. Daniels, Plymouth, MI (US); Kevin R. Ward, Superior Township, MI (US); Maryanne M. Collinson, Richmond, VA (US)

(73) Assignees: THE REGENTS OF THE UNIVERSITY OF MICHIGAN, Ann Arbor, MI (US); Virginia Commonwealth University, Richmond, VA (US)

( * ) Notice: Subject to any disclaimer, the term of this patent is extended or adjusted under 35 U.S.C. 154(b) by 0 days.

(21) Appl. No.: 16/564,917

(22) Filed: Sep. 9, 2019

(65) Prior Publication Data
US 2020/0003754 A1 Jan. 2, 2020

Related U.S. Application Data

(62) Division of application No. 15/030,958, filed as application No. PCT/US2014/061461 on Oct. 21, 2014, now Pat. No. 10,451,606.
(Continued)

(51) Int. Cl.
*G01N 27/327* (2006.01)
*G01N 33/49* (2006.01)
(Continued)

(52) U.S. Cl.
CPC ........ *G01N 33/49* (2013.01); *B01L 3/502707* (2013.01); *B01L 3/502715* (2013.01);
(Continued)

(58) Field of Classification Search
CPC ......... B01L 2200/12; B01L 2300/0645; B01L 2300/0896; B01L 2300/12;
(Continued)

(56) References Cited

U.S. PATENT DOCUMENTS 9,176,092 B2 * 11/2015 Kulmala ................ G01N 21/76
2002/0167322 A1 11/2002 He et al.
(Continued)

OTHER PUBLICATIONS

International Search Report and Written Opinion for Application No. PCT/US2014/061461, dated Feb. 13, 2015.
(Continued)

*Primary Examiner* — Lan Vinh
(74) *Attorney, Agent, or Firm* — Marshall, Gerstein & Borun LLP

(57) ABSTRACT

A bioelectrochemical sensor utilizing a nanoporous gold electrode. The bioelectrochemical sensor is suitable for measuring redox in biologic media while having increased resistance to biofouling as compared to conventional electrodes such as planar gold electrodes, due to greater exposed surface area of the three-dimensional ligature structure defining the nanopores. The nanopores have a pore size of 5-100 nm, preferably with an average pore size of less than 50 nm, and more preferably with an average pore size of less than 20 nm.

5 Claims, 9 Drawing Sheets

Related U.S. Application Data

(60) Provisional application No. 61/893,727, filed on Oct. 21, 2013.

(51) Int. Cl.
    *B01L 3/00* (2006.01)
    *G01N 27/30* (2006.01)
    *G01N 33/487* (2006.01)

(52) U.S. Cl.
    CPC ......... *G01N 27/301* (2013.01); *G01N 27/307* (2013.01); *G01N 27/3272* (2013.01); *G01N 27/3277* (2013.01); *G01N 27/3278* (2013.01); *G01N 33/48707* (2013.01); *B01L 2200/12* (2013.01); *B01L 2300/0645* (2013.01); *B01L 2300/0896* (2013.01); *B01L 2300/12* (2013.01); *G01N 2800/7009* (2013.01)

(58) Field of Classification Search
    CPC ......... B01L 3/502707; B01L 3/502715; G01N 27/301; G01N 27/307; G01N 27/3272; G01N 27/3277; G01N 27/3278; G01N 2800/7009; G01N 33/48707; G01N 33/49
    USPC ........ 216/83, 90, 91, 95; 204/403.1, 403.14, 204/403.13
    See application file for complete search history.

(56) References Cited

U.S. PATENT DOCUMENTS

| | | |
|---|---|---|
| 2004/0040416 A1 | 3/2004 | Erlebacher et al. |
| 2004/0140209 A1 | 7/2004 | Choi et al. |
| 2005/0136471 A1* | 6/2005 | Bhullar .............. G01N 27/3272 435/6.11 |
| 2008/0023325 A1* | 1/2008 | Mohapatra ............. C12Q 1/005 204/403.14 |
| 2008/0169191 A1 | 7/2008 | Krejci et al. |
| 2009/0297913 A1 | 12/2009 | Zhang et al. |
| 2014/0005492 A1* | 1/2014 | Harttig ............... A61B 5/14735 600/300 |
| 2016/0266090 A1 | 9/2016 | Daniels et al. |

OTHER PUBLICATIONS

Lee et al., "Fabrication and Optimization of a Nanoporous Platinum Electrode and a Non-Enzymatic Glucose Micro-sensor on Silicon," Sensors 2008, 8, 6154-6164.

Scanlon et al., Characterization of Nanoporous Gold Electrodes for Bioelectrochemical Applications, Langmuir 2012, 28, 2251-2261.

* cited by examiner

NANOPOROUS BIOELECTROCHEMICAL SENSORS FOR MEASURING REDOX POTENTIAL IN BIOLOGICAL SAMPLES

CROSS-REFERENCE TO RELATED APPLICATIONS

This is a divisional under 35 USC § 120 of U.S. application Ser. No. 15/030,959, issued as U.S. Pat. No. 10,451,606, which was the US national phase of International Application No. PCT/US14/61461, having an international filing date of Oct. 21, 2014, which claims the benefit of the filing date of U.S. Provisional Application No. 61/893,727, filed Oct. 21, 2013. Each of the priority applications, U.S. Ser. No. 15/030,959, PCT/US14/61461, and U.S. Provisional Application No. 61/893,727, is hereby incorporated by reference in its entirety.

FIELD OF THE DISCLOSURE

The present disclosure relates generally to performing redox potential measurements in biofouling solutions and, more particularly, to the formation and use of a nanoporous electrode, such as a nanopourous gold (Au) electrode, together with a reference electrode, such as an electroplated silver (Ag)/silver chloride (AgCl) reference electrode, in an electrochemical biosensor for making electrochemical (redox) measurements in biological fluids such as blood and serum.

BACKGROUND

The measurement of redox potential, or redox for short, is relatively simple in concept, requiring only a reference electrode and working electrode through which the balance of oxidants and reductants in any media can be measured via voltage (mV). However, historically there has been no reliable method to measure it due to biofouling (blockage of the electrode surface by proteins in biologic media), and consequently no rapid, reliable method for evaluating redox species and redox balance in metabolic and oxidative stress. Because of the inability to provide this direct measure of oxidative stress, current standards for evaluating the severity of these derangements in conditions such as sepsis and shock include only secondary measures of oxidative and metabolic stress, such as central venous oxygen saturation ($SvO_2$) and serum lactate measurements. These values are currently followed not only as indicators of the severity of the initial insult, but also as measures of the success of therapeutic interventions. Further, recent international guidelines define therapeutic endpoints based on the value of $SvO_2$, with saturations less than 70% indicating an ongoing metabolic and physiologic deficit necessitating an escalation of support.

Though these measures are the current standard, they have numerous limitations as they reflect only crude, averaged measures of the metabolic and clinical state, and provide only indirect measurements for directly relevant clinical data: cardiac output, oxygen metabolism, oxygen debt and overall oxidative stress. Even recent advances in regional tissue oxygenation measures, such as Near-Infrared Spectroscopy (NIRS) monitoring, can only measure regional oxygen saturations or serve as a non-invasive measure of $SvO_2$ that reports an oxygen saturation that may or may not be clinically relevant, but has no ability to reflect the true redox environment or oxidative stress present.

Furthermore, while there is much debate regarding antioxidant therapy in septic shock and critical illness, blood redox measurements can be useful in guiding such a therapeutic approach in the future. Pre-clinical studies have demonstrated the benefits of antioxidant therapy, such as the use of ascorbic acid in both attenuating the development of multiple organ dysfunction syndrome (MODS), and reducing the proinflammatory and procoagulant states that induce organ injury such as lung vascular injury in sepsis or after other insults such as trauma, cardiac arrest, or burns. There has been renewed interest in the role of Vitamin C, along with other antioxidants, in protecting against oxidative stress in ischemia/reperfusion injury and sepsis, including its ability to mitigate organ injury in these states. As speculated by multiple investigators, resuscitation fluids containing targeted anti-oxidant therapy may improve the ability to support patients with sepsis and protect against multiple organ dysfunction.

To accurately and reproducibly make electrochemical (redox) measurements in complex biologic fluid such as blood and plasma, the electrode must be able to exchange electrons, H+ ions, and oxygen free radicals with the redox species in solution. If the electrode surface is somehow modified or contaminated (e.g., by protein adsorption), then the electrode can lose its effectiveness as a redox sensor. The impact of biofouling on the electrochemical measurement will depend on the degree of modification and the redox species being detected. It is well known that when a conducting metal electrode is exposed to protein, adsorption will take place. To circumvent or reduce the impact of protein adsorption on the electrochemical activity of redox active molecules at the electrode surface, prior solutions have been to modify the electrode surface with, e.g., a pyridinethiol or polymer film (e.g., polyethylene glycol). Electrode modification, however, can impede electron exchange at the electrode surface and subsequently bias the results due to selective partitioning/exclusion of certain analyte species.

Another factor that becomes important, particularly with the potentiometric measurement of blood redox potential, is the reference electrode. In a potentiometric sensor, a high impedance voltmeter measures the potential of the indicator electrode with respect to the reference electrode.

The potential of the reference electrode stays constant during and between samples for the measured potential to reflect what takes place at the nanoporous electrode in solution. A common reference electrode to use is a standard commercial silver/silver chloride reference electrode (saturated potassium chloride (KCl)) with a porous Vycor frit. By fixing the concentration of potassium chloride, the potential of the reference electrode then becomes fixed. A fitted reference electrode, however, can also become clogged from the proteins/enzymes/cells in blood giving rise to a significant junction potential, and extreme cases, a sluggish, variable response. Because the contribution of the junction potential to the measured cell potential is not known, it is impossible to know the potential of the indicating electrode to any degree of accuracy.

The need for measuring redox at a direct measure of metabolic and oxidative stress is clear; however, there has been little progress in the field of redox measurements in complex biologic media. As noted above, the problem is that traditional planar (flat) metal electrodes cannot reliably or accurately make these measurements as they are fouled and rendered unresponsive in complex protein containing biologic solutions. Because of this, accurate measures for POC testing can be difficult. Furthermore, biofouling can prevent the development of a redox potential device capable of continuous or semi-continuous measurements of blood, urine, exhaled breath condensate, or tissue interstituium.

SUMMARY

Blood redox could serve as an easy, safe, and convenient point-of-care (POC) bedside test apt for real-time evaluation of shock, resuscitation, and organ dysfunction in a broad critical care population. In addition, POC redox measurements may offer guidance in diagnostic decision making, therapeutic interventions, and defining resuscitation endpoints in those patients most critically ill. Furthermore, redox measurements may be extended in the future to evaluate additional disease processes that are highly affected by reactive oxygen species (ROS) and changes in oxidative stress, such as acute lung injury, and in this case POC device development will prove invaluable in order to measure redox when only small fluid volumes are available, such as when evaluating exhaled breath condensate and in pediatric studies. In the end, we hope to establish redox as a biomarker in shock, resuscitation, and organ dysfunction and ultimately translate this work into a POC device for use at the bedside in order to improve outcomes in patients who are suffering from critical illness and injury, as well as those with disease states that are highly affected by redox balance.

In contrast to conventional secondary measurements, we propose that blood redox will give a real time, direct, and primary measure of the body's oxidative metabolism and metabolic needs in all phases of illness, including early-stage and progressive injury, and throughout ongoing resuscitation initially under highly controlled conditions. In this way, redox measurements might better reflect systemic oxygen debt, provide a true biomarker for gauging resuscitation effectiveness and endpoints, and may predict the risk of progressive organ dysfunction.

An electrochemical biosensor for making redox potential measurements is constructed utilizing a nanoporous gold (Au) electrode and a silver (Ag)/silver chloride (AgCl) reference electrode. This bioelectrochemical sensor can accurately and reproducibly measure the concentration of small redox active molecules in biologic media, such as blood and plasma, without surface modification of the electrodes, and is resistant to biofouling.

Because blood contains chloride ions, a silver-silver chloride coated silver wire as a reference electrode provides a reference electrode that is poised for use in an electrochemical biosensor for making electrochemical (redox) measurements in biological fluids such as blood and serum. The reference electrode will have a predictable value defined by the concentration of chloride in the biologic solution.

In contrast to conventional surface treatment of electrodes in electrochemical biosensors to avoid or reduce adverse affects of adsorption, involving modifying the electrode surface with a pyridinethiol or polymer film, the electrochemical biosensor requires no electrode modification, but instead relies on a properly defined pore structure. It is found that providing high surface area nanostructured electrodes can overcome many challenges associated with conventional electrochemical biosensors and are more resistant to biofouling, thereby providing reliable redox measurements in biologic media, including blood, urine, exhaled breath condensate, or the interstitium of tissue.

In one embodiment, nanopores are formed throughout the surface of a gold leaf by selectively etching silver from a gold/silver matrix with nitric acid, which dealloys the gold leaf. The result is a nanoporous (np) gold (Au) scaffold suitable for use as an electrode that can be used with a silver (Ag)/silver chloride (AgCl) reference electrode.

In another embodiment, nanopores are formed utilizing one or more co-sputter techniques, which are more standardized than etching with nitric acid, and enables the resulting nanoporous gold electrode to be directly integrated into a microfluidic chip.

The potentiometric measurement of blood redox potential using this arrangement is given by:

$E_{measured} = E_{np} - E_{ref}$

In the above formula, each of $E_{measured}$, $E_{np}$, and $E_{ref}$, which are voltages, are preferably in units of millivolts (mv). The governing equation for redox potential inherent in the cell (the biologic sample, e.g., fluid, blood, or other solution being measured) is given by the Nernst equation:

$$E = E^0 - \frac{0.05916}{z} \log 10 \frac{\alpha_{Red}}{\alpha_{Ox}}$$

$E_{cell}$=Cell Potential (electromotive force)
$E^\theta_{cell}$=Standard Cell Potential (influenced by temperature)
z=Number of Moles of Electrons transferred in the cell reaction
$\alpha_{Red}$=Chemical activity of the reductant species
$\alpha_{Ox}$=Chemical activity of the oxidant species The resulting nanoporous gold electrode has a surface area that is approximately 25 to 50 times larger than that of planar/flat gold, with nanopores that range from 5 to 50 nm in diameter, as measured via scanning electron microscopy. In addition, due to the nanoporous structure, the np gold electrodes, when compared to planar/flat electrodes, offer superior performance for electrochemical measurements in biofouling solutions by not only offering a much higher surface area, but also providing mass transport restriction. This mass transport restriction works by hindering large proteins from reaching the inner electrode surface, while allowing redox species and electrons access to the electrode via the nanoporous (np) structure.

The Ag/AgCl reference electrode has a diameter of, for example, 1 mm, and the gold electrode is approximately 4-5 mm×15-20 mm. The nanoporous gold electrode has a defined three-dimensional network of nanometer-sized pores and ligaments that are on the order of 20 nm. The size of the pores can be varied from about 5 to about 100 nm, depending on the dealloying conditions. Preferably, the nanoporous gold electrode has an average pore size of less than 50 nm. More preferably, the nanoporous gold electrode has an average pore size of less than 20 nm, as it is found that the smaller the pore size, the more effective the sensor in making redox potential measurements in biofouling-prone solutions, such as blood, urine, exhaled breath condensate, or the interstitium of tissue.

Further provided are methods of using the electrodes disclosed herein to monitor oxidative states of biological samples via redox potential. The biological sample can be, for example, blood, serum, urine, exhaled breath condensate, or tissue interstitium. The sample can come from a harvested organ (e.g., to monitor the organ's health prior to transplantation) or a blood product (e.g., from a blood bank) to monitor the blood product's viability prior to use in transfusion. The sample can come from a subject suffering from a metabolic or oxidative stress. The subject can suffer from multiple organ dysfunction syndrome (MODS), inflammation, ischemia/reperfusion injury, lung vascular injury, sepsis, trauma, cardiac arrest, burns, or shock. The subject can suffer from cardiogenic shock, neurogenic shock, distributive shock, septic shock, traumatic shock, hemorrhagic shock, burn shock, or hypovolemic shock. The redox potential of the sample (e.g., of the subject) can be measured over time to monitor the oxidative state of the sample. For example, progression of an oxidative disorder can be monitored using multiple redox potentials measured using an electrode as disclosed herein.

DETAILED DESCRIPTION OF THE PREFERRED EMBODIMENTS

Figure 1:
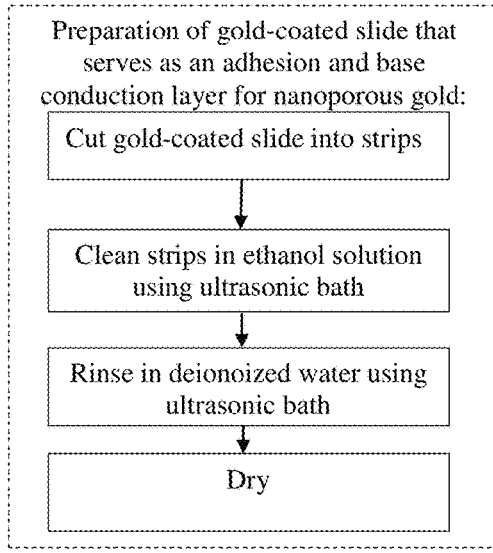
FIG. 1 is a flow chart schematically illustrating steps that may be employed to prepare a gold-coated slide that serve as an adhesion and base conduction layer for nanoporous gold, according to a technique of forming a nanoporous gold electrode for use in a bioelectrochemical redox sensor according to a first embodiment of the present disclosure, the technique of forming nanoporous gold including a nitric acid etching technique.

Although blood gas measures have long been established as a means to evaluate critical illness, they rely solely on pH and acid/base pairs in blood (proton chemistry) while the activity of the electrons has been relatively ignored (redox chemistry). It is the missing pieces, namely electron transfer and oxidation/reduction balance, that provide a more comprehensive evaluation of metabolic and oxidative stress in critical illness. Further, restoring redox balance is widely considered to be important for improving the metabolic derangements in shock. Moreover, oxidative stress is not merely a secondary phenomenon, but a central factor in driving the systemic inflammatory response leading to multiple organ failure. Due to a lack of reliable methods to directly measure blood redox state, it was necessary to rely upon secondary measures (such as lactate and $SvO_2$) to assess whether a patient is in oxidative stress. However, given the prevalence of sepsis and other adverse affects of oxidative stress, in patients having normal vital signs and stable secondary measures lactate and $SvO_2$, it would be desirable to supplement or even replace those secondary measurements with the methodologies described herein for directly evaluating changes in redox balance, in real time. In other words, with a better understanding and calibration of the association of redox balance with shock and progression to organ dysfunction, redox can be developed as a viable biomarker for shock, resuscitation (including fluid and transfusion requirements), regulation of coagulation, and organ dysfunction in critical illness and injury, as well as other disease states. Such tools can even be considered for continuous monitoring of harvested organs to improve preservations by monitoring the organ itself and organ preservation media.

One advantage of measuring redox balance to monitor metabolic and oxidative stress is that it directly reflects three biochemical states: pH, electron transfer, and oxidation-reduction reactions. Although blood gas measures have long been established as a means to evaluate critical illness, they rely solely on pH and acid/base pairs in blood (proton chemistry), ignoring the electrons and reactive oxygen species that provide a more comprehensive evaluation of metabolic and oxidative stress in critical illness. However, conventional redox sensors were too susceptible to biofouling to be effective for clinically-significant data collection or patient monitoring. By increasing the surface area of the precious metal or other active material of the working electrode through which the balance of oxidants and reductants in a biologic media (such as blood, plasma, urine breath condensate, or tissue interstitium) is measured in a redox sensor, the sensor's resistance to biofouling is increased.

The bioelectrochemical redox sensors of the present disclosure utilize high surface area, nanostructured electrodes. In particular, through the formation of nanopores throughout the surface of a precious metal, such as gold, as the working electrode of a bioelectrochemical redox sensor, with nanopores ranging from 5 to 50 mn in diameter, the resulting electrode has a surface area approximately 25 to 40 times larger than planar (flat) gold. In addition to increased resistance to biofouling, the nanoporous structure of the gold electrodes enhances the resulting sensor's mass transport restriction. This mass transport restriction works by hindering large proteins from reaching the inner electrode surface, while allowing redox species and electrons access to the electrode via the nanoporous structure. Electron transfer and redox species are hindered at the planar/flat gold surface of a conventional planar gold electrode of a conventional redox sensor by interference with albumin and proteins, whereas these albumin and proteins, while still present on a nanoporous gold (np Au) electrode, are sufficiently spread out so as not to block the nanoporous matrix and therefore cannot impede electron transfer and redox species exchanging with the bioelectrochemical redox sensors of the present disclosure.

Example 1

Figure 2:
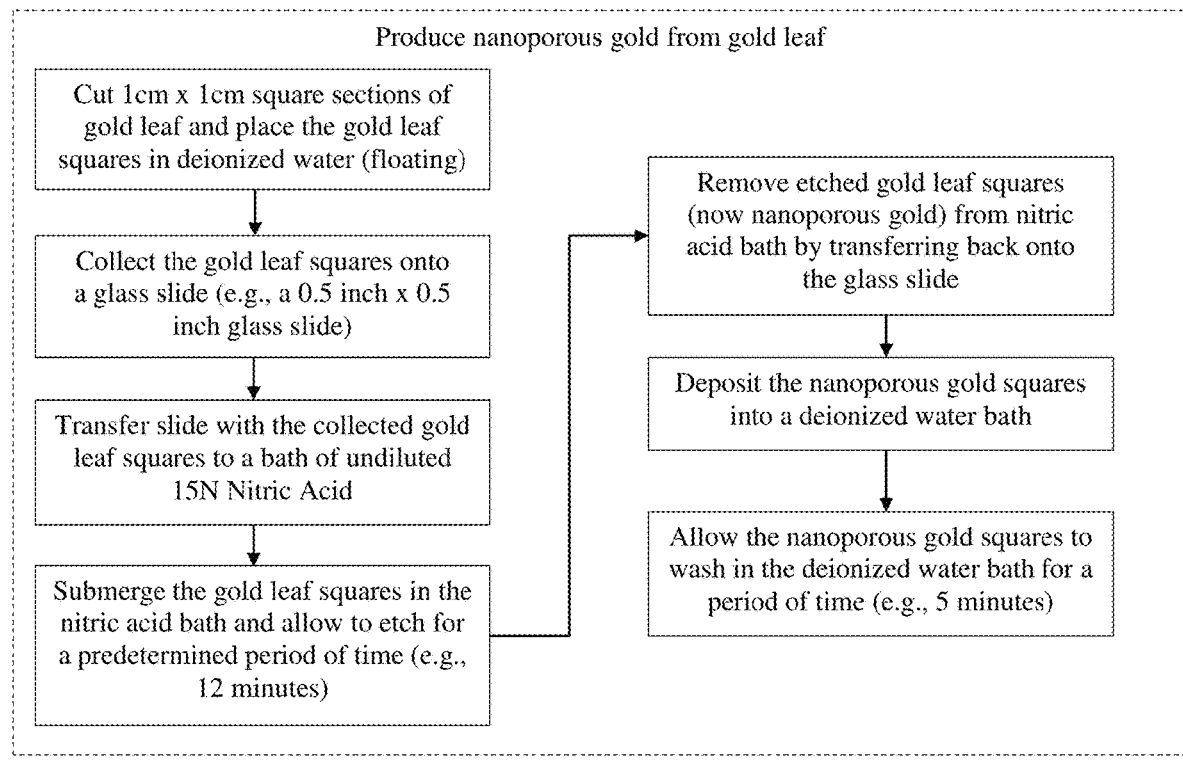
FIG. 2 is a flow chart schematically illustrating steps that may be employed to produce nanoporous gold from a gold leaf, for use in the formation of a nanoporous gold electrode for use in the bioelectrochemical redox sensor according to the first embodiment of the present disclosure.
Figure 3:
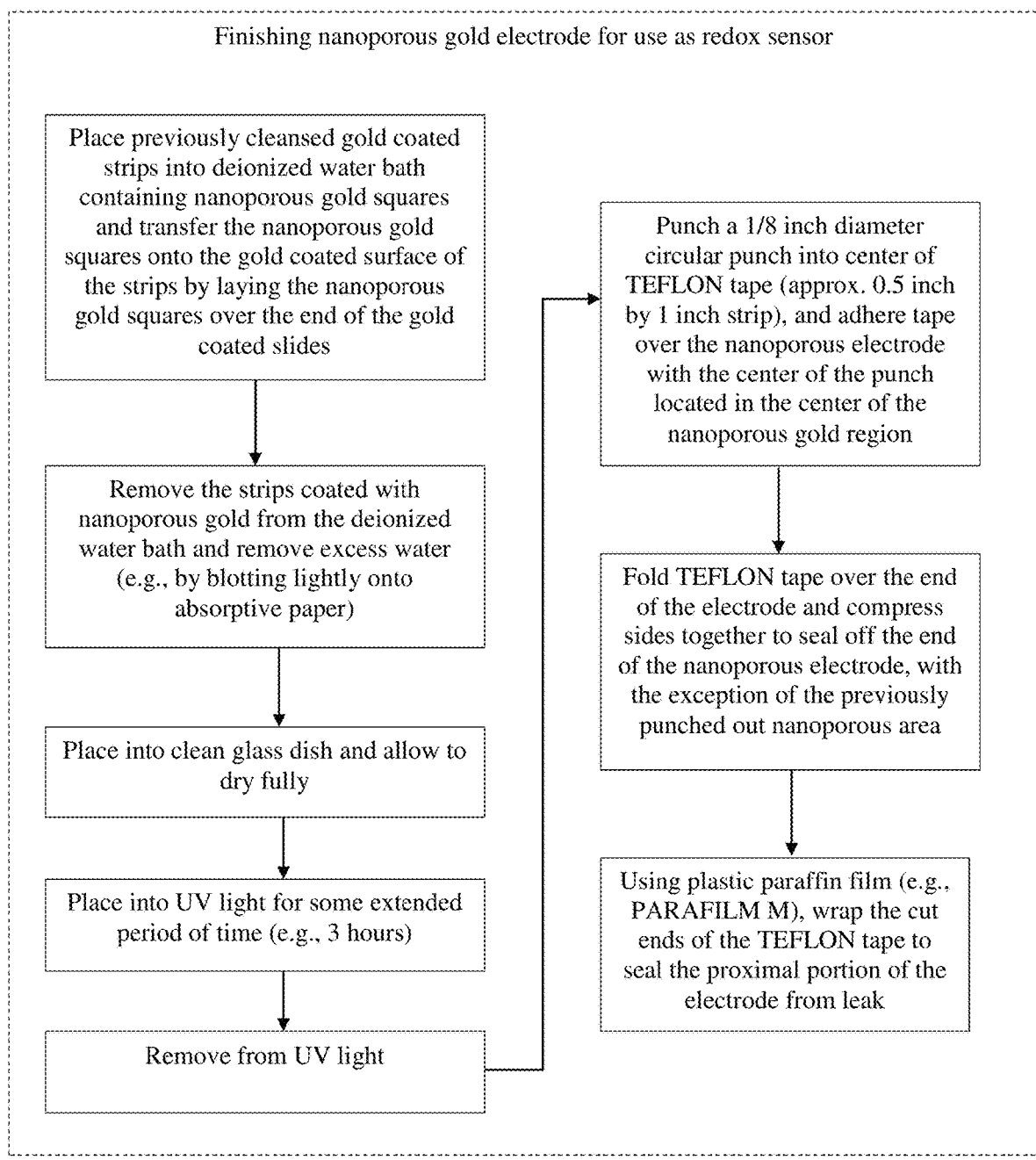
FIG. 3 is a flow chart schematically illustrating steps that may be employed to complete the nanoporous gold electrode for use in the bioelectrochemical redox sensor according to the first embodiment of the present disclosure.

A nanoporous gold electrode suitable for use in a bioelectrochemical redox sensors of the present disclosure was prepared by etching a gold leaf, following the protocol schematically illustrated in the flow charts of FIGS. 1-3. First, a gold-coated slide was prepared that served as an adhesion and base conduction layer for nanoporous gold. Then, nanoporous gold leafs were prepared using a process that involved etching gold leaf squares in nitric acid. Next, the nanoporous gold leafs were finished and formed into a nanoporous gold electrode. These steps will now be described in greater detail.

In preparing a gold-coated slide to serve as an adhesion and base conduction layer for nanoporous gold, as depicted in FIG. 1, we cut gold-coated microscope slides into strips approximately 2.5 cm (1 inch) in length×0.5 cm (0.2 inch) in width. Next, the microscope slides were cleaned in ethanol solution for 10 minutes using an ultrasonic bath. Subsequently, the gold-coated microscope slides were rinsed in deionized water for 10 minutes using an ultrasonic bath. The gold-coated microscope slides were then allowed to dry while the nanoporous gold was prepared using a nitric acid etching technique, as described below.

Starting with a 10-12 K white gold leaf (Monarch brand), as depicted in FIG. 2, the gold leaf was cut into 1 cm×1 cm square sections, and those cut-out gold leaf squares were placed, floating, into deionized water. Next, the gold leaf squares were collected onto small glass slides, which slides were previously cut to approximately 0.5 inch×0.5 inch, and transferred to an undiluted 15N nitric acid bath. The gold leaf squares were submerged in the nitric acid bath and permitted to etch therein for 12 minutes. Etching the gold leaf squares in nitric acid de-alloyed the gold leafs, with nanoporous gold remaining. Next, the etched gold leaf squares were carefully removed from the nitric acid bath by transferring the etched gold leaf squares, which, as a result of the nitric acid etching, were then nanoporous gold squares (np Au), onto the small glass slides. The nanoporous gold squares were then carefully transferred from the small glass slides into a deionized water bath. The nanoporous gold squares were washed in the deionized water bath for 5 minutes.

The steps for finishing the nanoporous gold electrode will now be described with reference to FIG. 3. The un-etched gold coated slide was placed into the deionized water bath containing the nanoporous gold squares. Using forceps, the nanoporous gold squares were picked up onto the gold coated surface of the strip by laying the nanoporous squares over the end of the pre-cut gold coated slide.

Next, the gold coated slide carrying the nanoporous gold was removed from the deionized water bath and blotted lightly onto absorptive paper to remove excess water, then placed into a clean glass dish and allowed to dry fully.

Once dry, the gold coated slide carrying the nanoporous gold was placed into ultraviolet (UV) light for three hours for further cleaning and treatment, then removed from the UV light. A ⅛-inch diameter circular punch was then punched through the center of a 0.5 inch×1 inch strip of TEFLON® tape, and the TEFLON® tape was then adhered over the UV-treated gold coated slide carrying nanoporous gold (i.e., the nanoporous gold electrode), with the center of the punch located in a center of the nanoporous gold region of the electrode. Next, TEFLON® tape was folded over the end of the electrode and the sides of the TEFLON® tape were compressed together to seal off the end of the electrode, with the exception of the previously punched out nanoporous area. Lastly, the cut ends of the TEFLON® tape were wrapped using a plastic paraffin film (PARAFILM M®) to seal a proximal portion of the nanoporous gold electrode from leakage.

Figure 10:
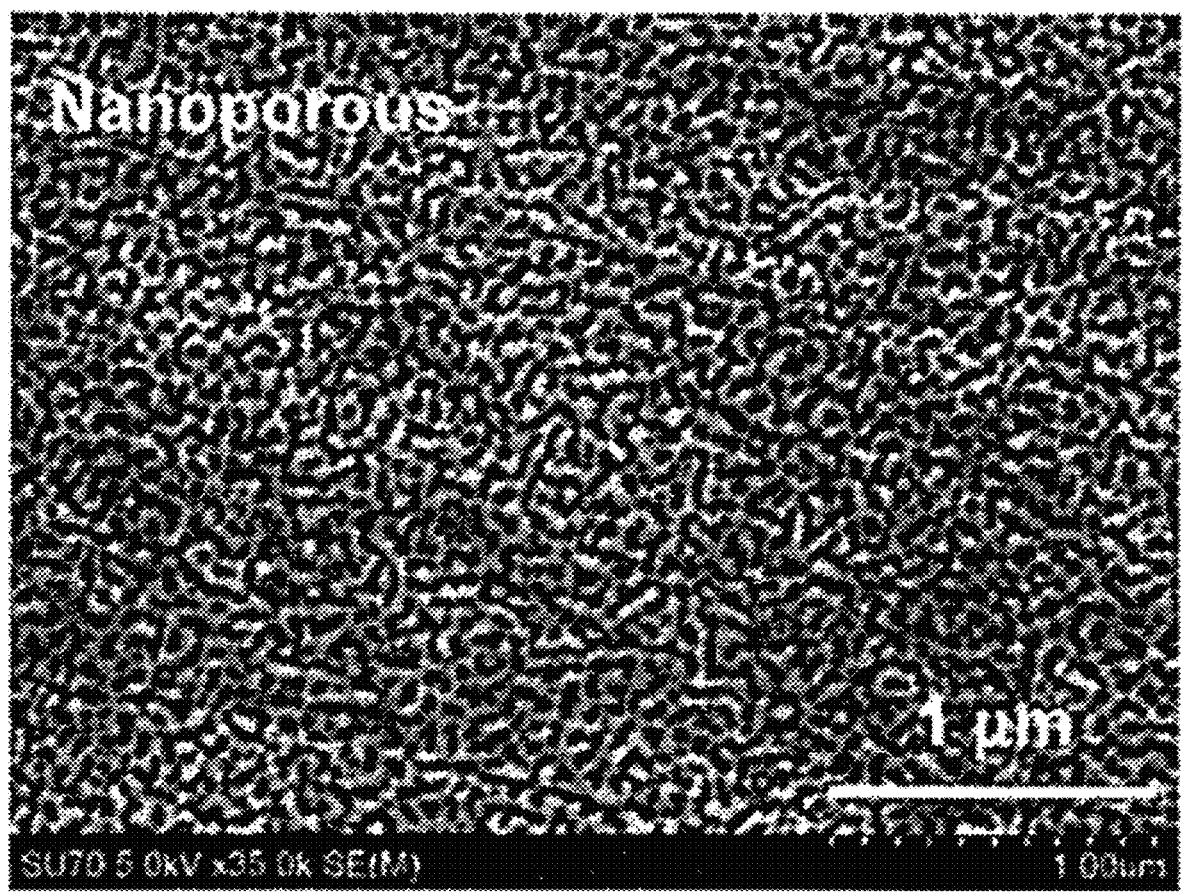
FIG. 10 is a scanning electron microscope (SEM) image of the surface of a nanoporous gold electrode prepared according to the nitric acid etching technique according to FIGS. 1-3 and is similar in structure to that produced according to the co-sputter method of FIG. 4.

A silver/silver chloride (Ag/AgCl) reference electrode was formed by electroplating AgCl on a Ag wire. The diameter of the Ag/AgCl reference electrode was 1 mm. By comparison, the dimensions of the nanoporous gold electrode were about 4-5 mm×15-20 mm. The average size of the nanopores was measured using a scanning electron microscope (SEM), and the average pore size was 20-30 nm. An SEM image of the nanoporous gold electrode is provided at FIG. 10, with a bar scale reference of 1 µm provided in the lower right corner (with 1 µm=1,000 nm).

Figure 11:
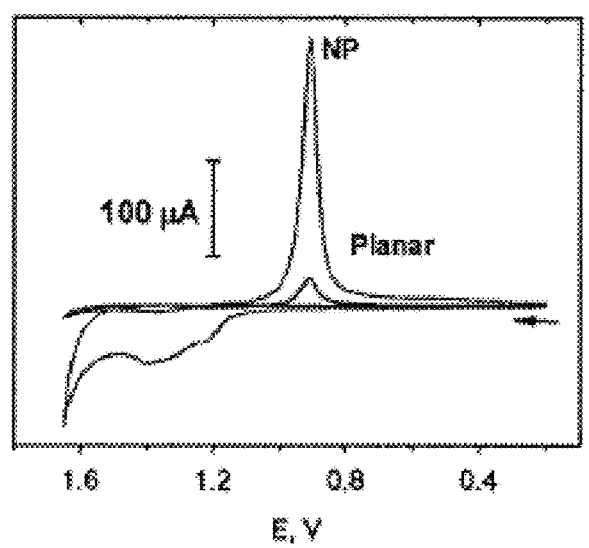
FIG. 11 is a cyclic voltammogram comparing a nanoporous gold electrode to a planar gold electrode in 0.5 M $H_2SO_4$ at 50 mV/s.

The surface area of the nanoporous gold electrode was measured by immersing the electrode in 0.5 M $H_2SO_4$, followed by cyclic voltammetry at 50 mV/s. The charge required to reduce the gold oxide formed during the oxidation step was measured and a conversion factor of 386 µC/cm$^2$ used to determine the real area of the exposed region of the electrode. FIG. 11 shows the cyclic voltammetric curve obtained for a nanoporous gold electrode formed according to the techniques and methods of the present disclosure, as compared to a conventional planar gold electrode. The ratio of the geometric area to the real area for the nanoporous gold electrode was 25.

Example 2

Figure 4:
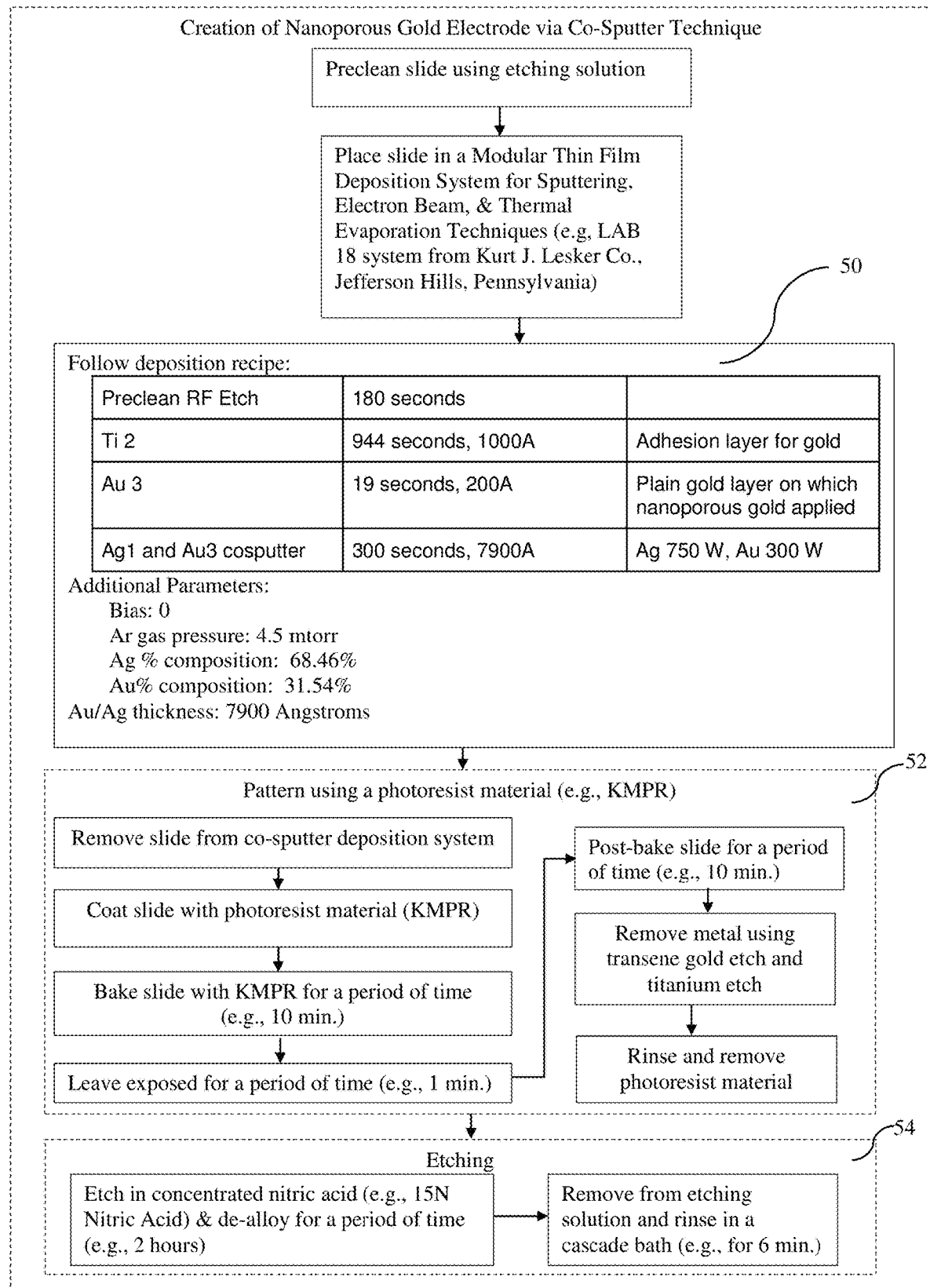
FIG. 4 is a flow chart schematically illustrating steps that may be employed to produce a nanoporous gold electrode according to a technique of forming a nanoporous gold electrode for use in a bioelectrochemical redox sensor according to a second embodiment of the present disclosure, the technique of forming nanoporous gold being dominated by a co-sputter technique.

A nanoporous gold electrode suitable for use in a bioelectrochemical redox sensors of the present disclosure was prepared using a co-sputter technique, following the protocol schematically illustrated in the flow chart of FIG. 4. The co-sputter technique creates much more reliable nanoporous gold matrices by co-depositing gold with silver and subsequently de-alloying this well-defined matrix by treating with nitric acid. In order to produce nanoporous gold electrodes through this process, titanium is used as an adhesion layer to apply pure gold to a glass or silica base and the co-sputtered Ag/Au matrix is applied on top of these layers. Final production of the electrode involves patterning for integration into a microfluidic cartridge, by etching away defined patterns of the deposited materials using a photoresist material and subsequent treatment with transene gold and titanium etch. This technique was performed using a Modular Thin Film Deposition System for Sputtering, Electron Beam, & Thermal Evaporation Techniques, namely the LAB 18 system from Kurt J. Lesker Co., Jefferson Hills, Pa.

Glass slides were precleaned using an etching solution. These slides were then placed in the LAB 18 system. The LAB 18 system was operated according to the deposition recipe and additional parameters identified in Box 50 of FIG. 4. As depicted at Box 52, the slides were removed from the LAB 18 co-sputter deposition system, then the slides were coated with KMPR photoresist material. Next, the photoresist-coated slides were baked for 10 minutes, left exposed for 1 minute, then post-baked for 10 minutes. Unwanted metals deposited on the slides during the co-sputtering technique were then etched away with transene gold etch and titanium etch. Next, the slides were rinsed and placed in REMOVER PG (a photoresist remover) for 15 minutes to remove the KMPR photoresist material. As depicted at Box 54 of FIG. 4, the slides were then etched in 15N Nitric Acid and de-alloyed for 2 hours, after which they were removed and rinsed in a cascade bath for 6 minutes. Each resulting nanoporous gold electrode was then ready to be paired with a reference electrode, such as an Ag/AgCl reference electrode, for use in a bioelectrochemical redox sensor and integrated into a microfluidic cartridge for point-of-care measurement.

Figure 14:
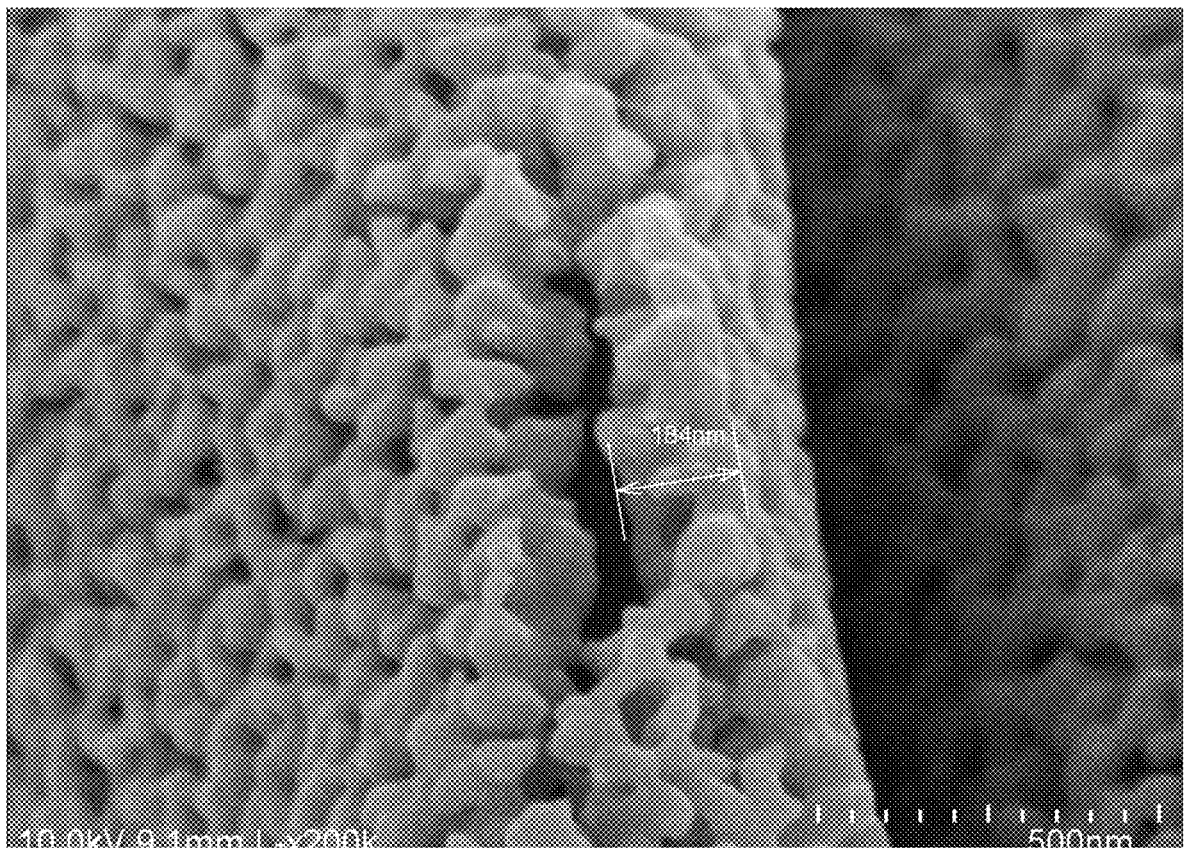
FIG. 14 is an SEM image of the surface of a nanoporous gold electrode prepared according to the co-sputter technique with nitric acid de-alloying according to FIGS. 4 and 6-9, with pore size in the range of 20-30 nm.

Co-sputter formation of nanoporous gold electrodes provides the ability to control thickness of the electrode, which can vary based on the particular application. The greater the thickness, the greater the sensitivity of the electrode, as the thicker the electrode, the thicker the ligaments of the three-dimensional network of nanometer-sized pores and ligaments defining the nanoporous gold electrode, and thus the greater exposed surface area. However, even a relatively thin nanoporous gold electrode is acceptable for performing redox measurements on solutions, as even thin nanoporous gold electrodes are sufficiently resistant to biofouling. An SEM image of a nanoporous gold electrode produced according to the co-sputter technique with nitric acid de-alloying according to the method depicted in FIG. 4 is provided at FIG. 14. The nanoporous gold electrode illustrated in FIG. 14 has a pore size in the range of 20-30 nm.

Figure 5:
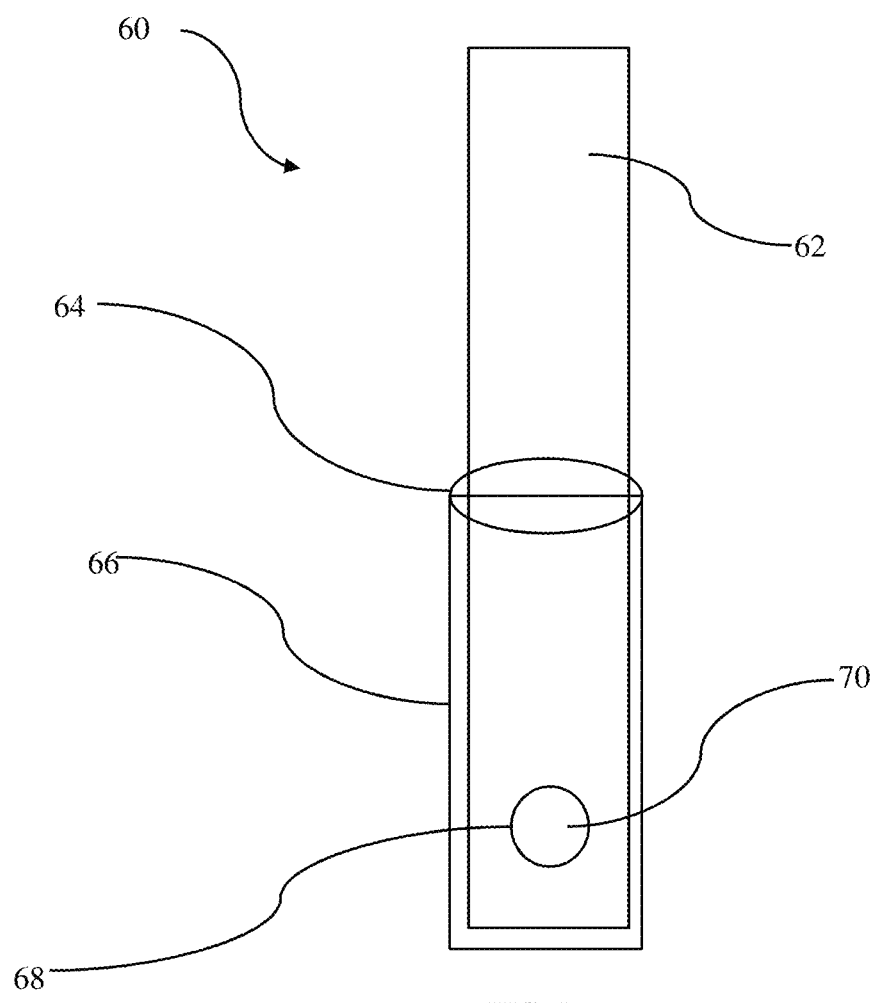
FIG. 5 is a top view of a nanoporous gold electrode for use in a bioelectrochemical redox sensor according to the present disclosure.

Turning to FIG. 5, a nanoporous gold electrode 60 is illustrated. Nanoporous gold electrode 61 includes a gold coated slide 62 (which, by way of example only, has a length of 2.5 cm), a plastic paraffin film (PARAFILM) wrap 64, and a TEFLON® tape cover 66 over at least a portion of the gold coated slide 62 that has been processed to form the nanopores therein. The TEFLON® tape cover 66 (extending a length, by way of example only, of 1.25 cm) has a ⅛-inch punch-out 68 therein, the punch 68 exposing a nanoporous gold region 70 of the gold coated slide 62, the exposed nanoporous gold region having a radius of 1/16-inch or 0.159 cm.

Figure 6:
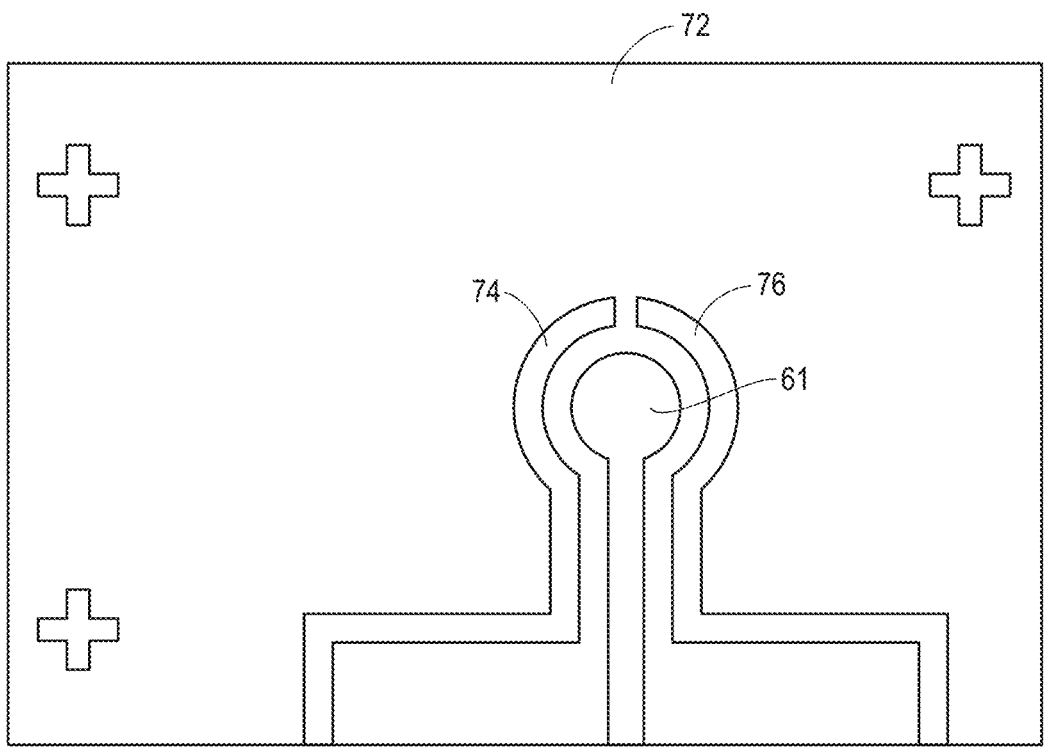
FIG. 6 is a top view of a bioelectrochemical redox sensor according to the present disclosure, including a nanoporous gold electrode.

FIG. 6 illustrates the nanoporous gold electrode 61, produced by the co-sputter technique described in Example 2, incorporated into a bioelectrochemical sensor 72. A reference electrode 74, such as an Ag/AgCl reference electrode, is disposed approximately 1 mm from the nanoporous gold electrode 60. A counter electrode 76, such as a platinum (Pt) auxiliary electrode, is disposed approximately 1 mm from the nanoporous gold electrode 61 on an opposite side of the nanoporous gold electrode 60 from the reference electrode 74.

Figure 7:
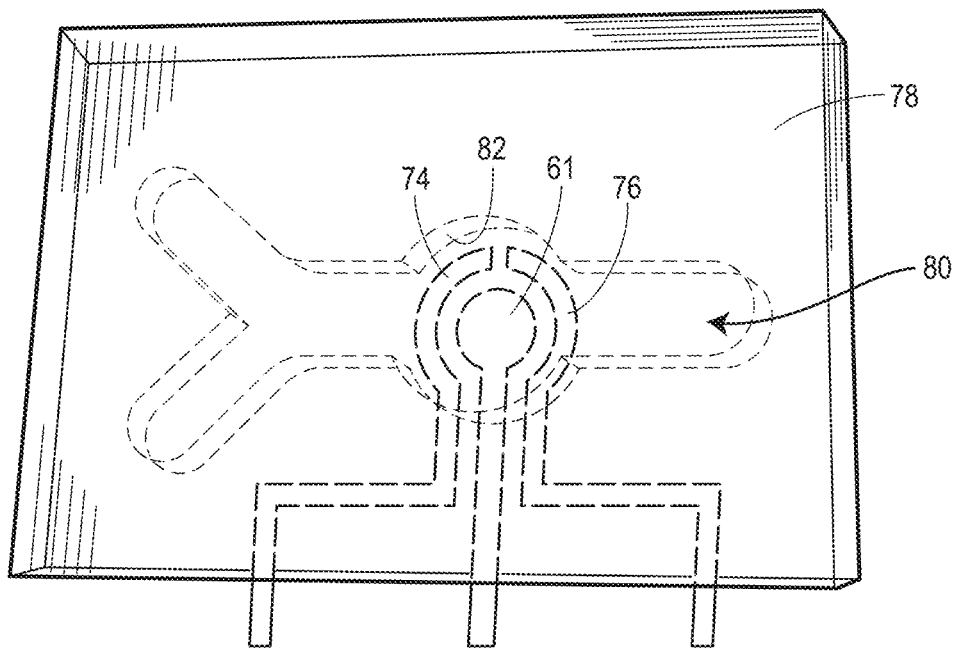
FIG. 7 is a top view of the bioelectrochemical redox sensor of FIG. 6, in combination with an electrode mask having a microfluidic channel formed therein, the microfluidic channel including a bulbous portion aligned with the nanoporous gold electrode.
Figure 8:
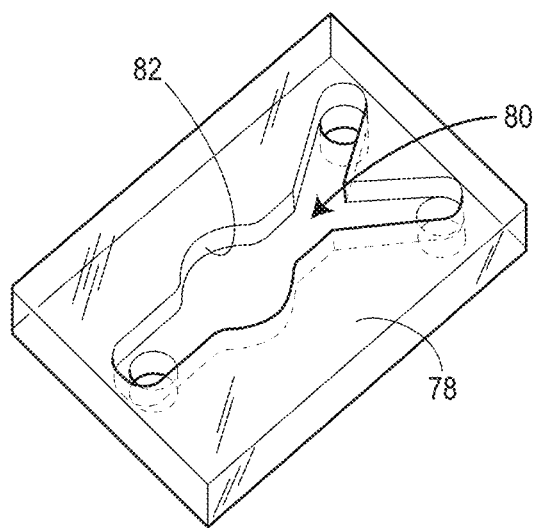
FIG. 8 is a bottom view of the electrode mask of FIG. 7.
Figure 9:
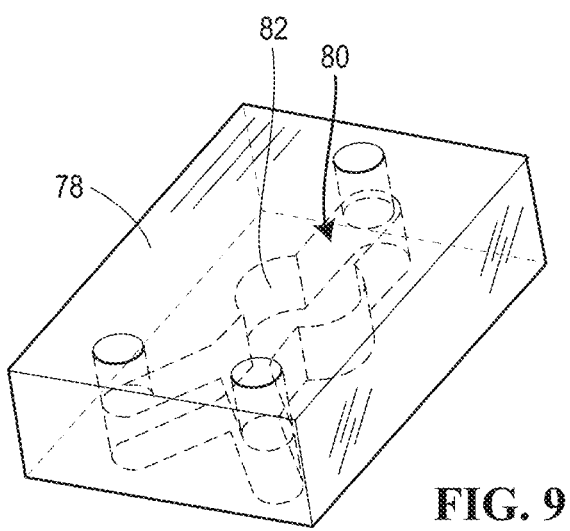
FIG. 9 is a top view of the electrode mask of FIG. 8.

FIG. 7 illustrates a bioelectrochemical sensor 72 such as that illustrated in FIG. 6, together with a block 78 having a microfluidic channel 80 formed therein. The block 78 may be made of Polydimethylsiloxane (PDMS) or other material that is air impermeable, such as a hybrid polyethylene-terephthalate (PETG)-polyurethane (PU) material. The microfluidic channel 80 is generally Y-shaped, and has a bulbous region 82 that, when the block 78 is placed into registration with the bioelectrochemical sensor 72, aligns with the exposed nanoporous gold region 70 of the nanoporous gold electrode 61. Together, these components integrated together form a microfluidic redox sensing cartridge, or platform, that enables very small volumes (<150 microliter) to be tested, and allows for point-of-care measurements when coupled with a portable potentiostat. FIGS. 6-9 serve as an example of this process and may also be performed in the future through integration with indwelling catheters and other devices and hardware.

Example 3

Figure 12:
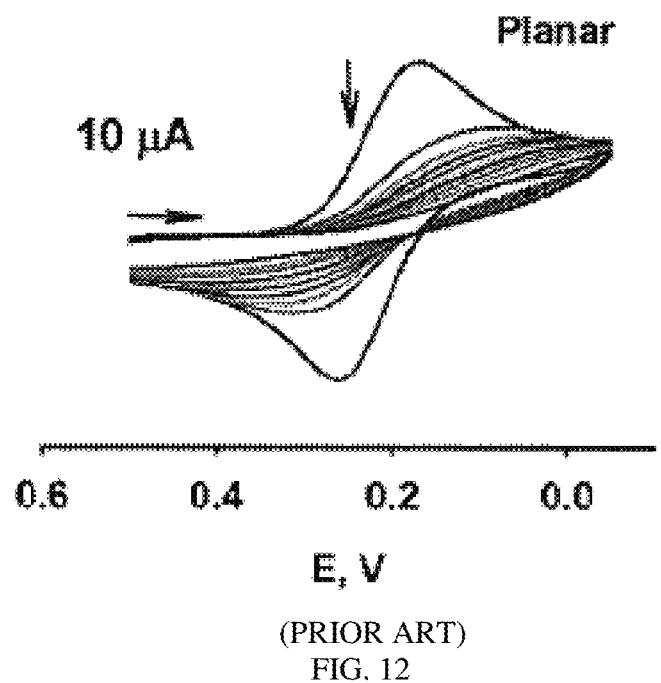
FIG. 12 is a plot of a plurality of superimposed cyclic voltammetry curves for a conventional planar gold electrode in a solution containing potassium ferricyanide, over a time-lapsed series of voltage measurements before and after addition of bovine serum albumin, over the course of 60 minutes, illustrating the planar gold electrode's degradation in measurement capability due to biofouling.
Figure 13:
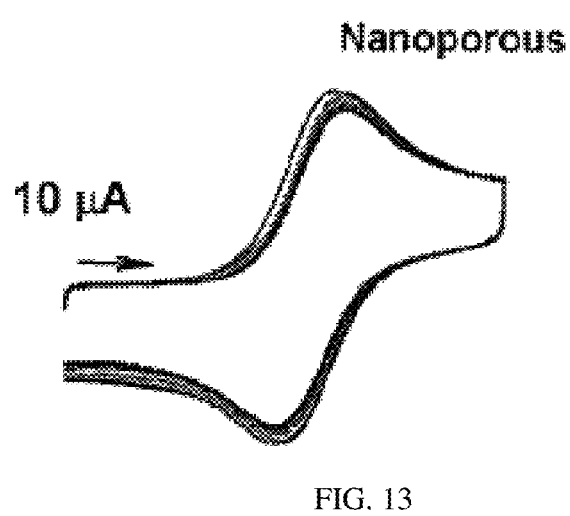
FIG. 13 is a plot of a plurality of superimposed cyclic voltammetry curves for a nanoporous gold electrode prepared according to the methods depicted in FIGS. 1-3 of the present disclosure in a solution containing potassium ferricyanide, over a time-lapsed series of voltage measurements before and after addition of bovine serum albumin, over the course of 60 minutes, illustrating the nanoporous gold electrode's low degredation in measurement capability (as compared to that of the conventional planar gold electrode as illustrated in FIG. 12), illustrating a greater resistance to biofouling.

To demonstrate the superiority in resistance to biofouling of nanoporous gold electrodes in biologic media as compared to conventional planar gold electrodes, cyclic voltammetry (CV) was performed on both a nanoporous gold electrode formed according to the nitric acid etching technique depicted in FIGS. 1-3 and as described in Example 1, and a planar gold electrode. Each electrode was placed in a solution containing potassium ferricyanide ($Fe(CN)_6^{3-}$), a common redox probe, and then bovine serum albumin (BSA) was added while making serial measurements over a period of 60 minutes. CV data was collected prior to addition of BSA, as well as at about 1 minute after addition of BSA, 2, 5, 8, 12, 16, 20, 30, 40, and 60 minutes after addition of BSA. As shown in FIGS. 12 and 13, before addition of BSA, ferricyanide exchanges electrons rapidly with the electrode surface of both electrodes, as evident from the shape of the CV (although current and sensitivity is greater in the nanoporous electrode). However, after addition of BSA, the CV at the planar Au electrode changed dramatically, becoming blocked (biofouled) while the CV at the nanoporous Au electrode did not. Adsorption of plasma proteins coupled with surface fouling significantly alter the electron exchange rates of the various redox species present and affect the accuracy and precision of the measurement of redox potential. In addition, current was measured via both electrodes throughout the observed time frame, and not only did the current drop significantly over time in the planar electrode, but there was larger variation in planar electrode redox measurements as indicated in the inset graph.

Example 4

The experiment of Example 3 was replicated using human whole blood instead of BSA, and similar results as depicted in FIGS. 12 and 13 were obtained.

Example 5

Swine were hemorrhaged to varying degrees of oxygen debt (up to 80 cc/kg) and then resuscitated. Matched redox potential measurements were then made using a nanoporous gold electrode formed according to the nitric acid etching technique depicted in FIGS. 1-3 and as described in Example 1. The redox potential measurements were made during hemorrhage and throughout resuscitation, and compared with oxygen debt. The data indicated a correlation between redox potential and oxygen debt, with blood redox becoming more negative with accumulating oxygen debt, and recovering back toward baseline throughout resuscitation. This serves to demonstrate that redox measurements not only reflect a real time assessment of progressing shock (such as that present in septic shock), but that redox is truly a primary and direct measure of oxidative stress and oxygen debt. In addition, although all physiologic parameters appeared within normal limits at end resuscitation in this experiment, including $SvO_2$, redox potential had not yet returned to baseline, suggesting ongoing oxidative stress and improper redox balance, which may indicate that redox measurements may better signal inadequate resuscitation and thus act as a biomarker for gauging resuscitation and therapeutic intervention in patients with sepsis and septic shock.

There are a wide variety of potential applications of redox monitoring with bioelectrochemical redox sensors having nanoporous electrodes according to the methods, techniques, and apparatus of the present disclosure, both in vivo and ex vivo. In particular, redox measurements may be made in a wide variety of blood and biologic fluids including, but not limited to, whole blood, including plasma, serum, any other fluid component of blood; respiratory fluids and vapor, including sputum, exhaled breath condensate, bronchial alveolar lavage fluid, and condensate or exhaled volume from a ventilator circuit (for patients receiving either invasive or non-invasive mechanical ventilation; urine (either clean catch, via intermittent catheterization, or via a Foley or other indwelling catheter); cerebral spinal fluid, including fluid taken from ventricular system of the brain or other fluid collection within or surrounding the brain/skull; exudative and/or transudative fluid (from any source), including pleural fluid, peritoneal fluid, abscess or other fluid collection secondary to suspected infection, serous fluid collections from any source, or other body fluid collection. In addition, continuous or semicontinuous monitoring of these fluids and even tissue interstitium within organs themselves would be possible when biofouling is minimized.

Additionally, redox measurements may be made using bioelectrochemical redox sensors according to the present disclosure in a wide variety of non-biologic fluids utilized for clinical purpose or personal health, including, but not limited to, intravenous fluids (saline, albumin, Dextrose, TPN, and combinations of these fluids+/−Electrolytes), dialysis solution utilized in peritoneal and hemodialysis as well as ultrafiltrate and fluids utilized in continuous renal replacement therapy (CRRT), pharmaceutical solutions and drugs used to treat patients (all liquid/solution preparations), and any other liquid or solution that does not erode the electrode surface (i.e. strong acids).

There are a wide variety of clinical and non-clinical uses for the bioelectrochemical redox sensors according to the present disclosure, including, but not limited to, sepsis and septic shock, all forms of systemic shock (such as cardiogenic, neurogenic, distributive, septic, traumatic/hemorrhagic/burn, and hypovolemic), cardiovascular disease/heart disease; lung disease and acute lung injury, such as COPD/emphysema, asthma, pneumonia, cystic fibrosis, and acute respiratory distress syndrome, diabetes including diabetic ketoacidosis, acute and chronic kidney injury and renal disorders of all types, traumatic brain injury and other brain injured states, including epilepsy/status epilepticus and stroke, clinical oncology and hematology including sickle cell disease, gastrointestinal diseases such as inflammatory bowel diseases, pharmaceutical monitoring, trauma and burn management, monitoring of blood in blood banks for blood product viability, safety, and treatment with antioxidants, transplant organ viability and optimization, and any other condition affected by oxidative metabolism, oxidative stress, reactive oxygen species, oxygen free radicals or other biochemical/electrochemical processes that involve oxidation-reduction reactions and redox pairs.

A bioelectrochemical redox sensor having a nanoporous gold electrode according to the present disclosure may be provided as a point-of-care device similar to a glucometer or bedside blood gas analyzer (e.g. i-STAT® blood gas analyzer), including a disposable microfluidic testing cartridge, such as that described in Example 2, that would contain the integrated nanoporous gold electrode coupled with a handheld potentiostat reader with an imbedded screen for result reporting. Alternately, it could transmit results to a remote display, such as a computer, a tablet, or a smartphone. As a handheld, portable device, the bioelectrochemical redox sensor device could be deployed both in and out of the hospital setting and utilized in multiple environments from the battlefield to the ICU to the general medical care setting. Additionally, a bioelectrochemical redox sensor having a nanoporous gold electrode according to the present disclosure may be provided as part of a continuous or semicontinuous device to measure redox potential of the central circulation for example as a part of a central venous or arterial catheter, as part of an extracorporeal device such as a dialysis unit, cardiopulmonary bypass, or extracorporeal membrane oxygenation device, as part of a urinary catheter device for measuring urine, as part of a ventilator circuit for exhaled breath condensate, as part of a ventriulostomy device for cerebrospinal fluid, as part of an indwelling tissue probe for tissue parenchymal interstitial, as part of a tissue preservation apparatus for organ preservation, and others.

Automated treatments could be devised based on measurements of redox potential employing the reliable, biofouling-resistant nanoporous gold electrode-based bioelectrochemical sensors of the present disclosure, similar to artificial pancreas or glucose/insulin management. For instance, redox measurement-based treatment systems could utilize a controller in communication with a treatment delivery device and a biofouling-resistant nanoporous gold electrode-based bioelectrochemical sensors of the present disclosure, with a feedback loop, such that the controller, in real time, continuously adjusts the treatment delivery device based on redox measurements.

Given that redox measurements provide a primary and direct measure of vital clinical information, namely oxidative/metabolic stress and oxygen debt, clinicians may no longer need to rely on crude secondary measures to guide their management of patients with sepsis and septic shock. Instead, they can use redox measures as systemic or local biomarker, in real time, to identify the severity of sepsis/septic shock, evaluate the adequacy of resuscitation, guide therapeutic interventions, and monitor the patient's progress over time. By providing more accurate and rapid evaluation of the patient's condition, the redox platform may enable more accurate diagnostic evaluation and timely therapeutic intervention that could serve to improve outcomes and decrease both the health care costs and mortality associated with critical illness and injury, or any other disease processes disclosed herein.

What is claimed is:

1. A bioelectrochemical sensor, comprising:
   a first electrode including a nanoporous precious metal, the nanoporous precious metal of the first electrode being nanoporous gold, the first electrode including
   a plurality of gold coated strips;
   an etched gold leaf disposed over a surface of the plurality of gold coated strips;

a strip of TEFLON tape disposed over the etched gold leaf, the TEFLON tape having a hole therethrough positioned over the etched gold leaf;

a reference electrode, the reference electrode being a silver/silver chloride electrode; and a counter electrode, the counter electrode being platinum.

2. The bioelectrochemical sensor of claim 1, in combination with a block having a microfluidic channel therein, the microfluidic channel including a portion aligned with an exposed nanoporous region of the first electrode.

3. The bioelectrochemical sensor of claim 1, the pores of the nanoporous precious metal of the first electrode having a pore size of 100 nm or less.

4. The bioelectrochemical sensor of claim 3, the nanoporous precious metal of the first electrode having an average pore size of less than 50 nm.

5. The bioelectrochemical sensor of claim 3, the nanoporous precious metal of the first electrode having an average pore size of less than 20 nm.

* * * * *